United States Patent [19]

Rautenstrauch et al.

[11] 3,946,078
[45] Mar. 23, 1976

[54] CYCLOALIPHATIC UNSATURATED KETONES AS ODOUR- AND TASTE-MODIFYING AGENTS

[75] Inventors: Valentin Rautenstrauch, Grand-Lancy, Geneva; Ferdinand Näf, Geneva, both of Switzerland

[73] Assignee: Firmenich SA, Geneva, Switzerland

[22] Filed: Apr. 29, 1974

[21] Appl. No.: 465,082

Related U.S. Application Data

[62] Division of Ser. No. 284,467, Aug. 29, 1972, Pat. No. 3,852,355.

[30] Foreign Application Priority Data

Aug. 31, 1971 Switzerland.................... 12755/71

[52] U.S. Cl....... 260/586 R; 252/522; 260/346.1 R; 260/586 P; 260/611 R; 260/617 E; 260/631 R; 260/648 R; 426/650
[51] Int. Cl.$^2$......................................... C07C 45/00
[58] Field of Search ................................ 260/586 R

[56] References Cited
UNITED STATES PATENTS 3,822,315   7/1974   Klem et al. ........................... 260/586 R

FOREIGN PATENTS OR APPLICATIONS 2,022,216   5/1970   Germany ........................... 260/586

OTHER PUBLICATIONS

Klem et al., "Chem. Abstracts," Vol. 75, p. 151319K, (1971).

Primary Examiner—Norman Morgenstern
Attorney, Agent, or Firm—Pennie & Edmonds

[57]   ABSTRACT

Process for the preparation of unsaturated cycloaliphatic ketones useful as perfuming and odour-modifying agents in the manufacture of perfumes and perfumed products, and as flavouring and taste-modifying agents in the aromatization of foodstuffs in general and imitation flavours for foodstuffs, beverages, animal feeds, pharmaceutical preparations and tobacco products.

Compositions of matter relating to some of said unsaturated cycloaliphatic ketones which are new, and perfume- and flavouring compositions containing same.

4 Claims, No Drawings

CYCLOALIPHATIC UNSATURATED KETONES AS ODOUR- AND TASTE-MODIFYING AGENTS

This is a division, of application Ser. No. 284,467 filed Aug. 29, 1972, now U.S. Pat. No. 3,852,355.

SUMMARY OF THE INVENTION

The invention relates to a new process for the preparation of unsaturated cycloaliphatic ketones having the formula

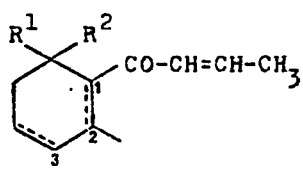

I containing an isolated double bond in position 1 or two conjugated double bonds in position 1 and 3 of the ring, the double bonds being represented by the dotted lines, and wherein the substituents $R^1$ and $R^2$ may be the same or different and each represents a hydrogen atom or a lower alkyl radical containing from 1 to 6 carbon atoms, which process comprises treating a diol of formula

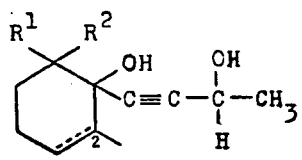

II comprising a saturated or mono-unsaturated six membered ring, the double bond being indicated by the dotted line, with an acidic dehydrating agent.

The invention relates further to a compound of formula

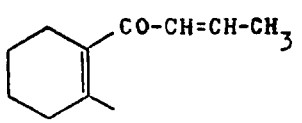

Ia and to its use as flavouring and perfuming ingredient, as well as to certain of the intermediates formed during the above process.

The present invention relates further to a new process for the preparation of unsaturated cycloaliphatic alcohols of a formula

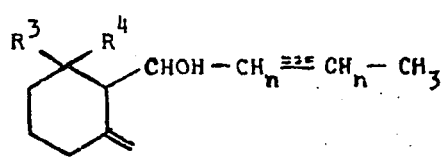

V containing a double or triple bond in the position indicated by the dotted lines and wherein the substituents $R^3$ and $R^4$ may be the same or different and each represents a lower alkyl radical containing from 1 to 6 carbon atoms, and the index n stands for zero or 1, which process comprises subjecting an ether of formula

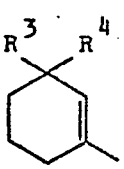

VI wherein the dotted lines and the symbols $R^3$, $R^4$ and $n$ have the same meaning as above, to a rearrangement by the action of a strong base and subsequently of a protic solvent.

The above mentioned compounds V possess interesting organoleptic properties and may be used as intermediates for the preparation of the corresponding ketones [see Swiss patents Nos. 521,099 and 509,399].

BACKGROUND OF THE INVENTION

One of the main objects of the aromatization of foodstuffs for instance is to restore the original quality and nature of the flavour, aroma and taste of a given foodstuff material. Very often in fact the organoleptic properties of foodstuffs particularly diminish or are somehow modified in the course of the processes of freezing and storage, or during the modifications, such as cooking or baking, to which the foodstuffs are subjected in order to yield an edible material.

In the past the aromatization was mainly achieved by using materials of natural origin. Nowadays, however, synthetic chemical compounds are used at an ever increasing rate. Said compounds possess the advantage of being available very often in unlimited quantities and at prices lower than those of the natural materials. Moreover, due to the fact that the flavouring character of a natural material is the result of the overall effect determined by the combination and interaction of each of its constituents, the effects achieved by said natural material are very often not as well reproducible as those obtained by the use of the pure synthetic compounds.

In the field of perfumery the man in the art has to solve a similar problem in attempting to reconstitute the olfactive notes of certain natural essential oils or extracts. The perfumer's creativity however is continually boosted by the finding of new synthetic compounds, the organoleptic properties of which will enable him to introduce unprecedented olfactive characters or nuances into new phantasy perfume compositions.

As a consequence, the problem that the chemical industry has to solve is to satisfy the increasing demand of organoleptically interesting chemicals in order to better suit the specific needs of flavourists and perfumers.

The process of the present invention provides a novel and technically original solution to the problem set by the synthesis of unsaturated cycloaliphatic ketones of formula I. These compounds have been prepared in the past by various synthetic methods which can be resumed as follows:

a. partial hydrogenation of the corresponding acetylenic derivatives [Swiss patent No. 498,795];
b. direct condensation of an organo-metallic derivative of propene with a cyclogeranyl derivative [Swiss patent No. 503,684];
c. cyclization of a "pseudo-ketone" by means of acidic cyclization agents [Swiss patent No. 503,685];
d. dehydrogenation of a cyclohexenic ketone to afford the corresponding cyclohexadienic derivative [Swiss patent No. 505,773].

The above indicated methods have the disadvantage of
i. affording the desired compounds only in poor yield and/or
ii. using non easily accessible starting materials.

The process of the present invention does not offer the said disadvantages and, as a consequence, it can be conveniently exploited by the chemical industry.

PREFERRED EMBODIMENTS OF THE INVENTION

As mentioned above, according to the invention compounds of formula I are prepared by treating a diol of formula II with an acidic dehydrating agent. A class of suitable acidic dehydrating agents comprises mineral or organic protonic acids such as phosphoric acid, sulphuric acid, trifluoroacetic acid or p-toluenesulphonic acid or acidic diatomaceous earths or an acidic cation exchange resin. For practical and economic reasons sulphuric acid is preferred.

We have observed that in the presence of derivatives of certain metals such as, for instance, copper, nickel or mercury salts, the yield of the final product was improved. To this effect it is preferred to use mercuric acetate.

The temperature at which the dehydrating reaction can be carried out may vary within wide limits. However, it has been observed that in order to obtain good yields of final product a temperature comprised between about 40° and about 90°C, preferably between 60° and 80°C, was convenient.

The concentration of the acid used can also vary within wide limits. In particular it is preferred to use an acid as defined above in an aqueous solution. If sulphuric acid is chosen as dehydrating agent, a concentration comprised between about 20 and 50 %, preferably 30 % (parts by weight), in water is conveniently used.

The diols of formula II used as starting materials in the process of the present invention can be prepared according to a known method [cf. e.g.: Pharm. Bull., 4, 85–88 (1956), as reported in Chem. Abstr., 51, 5007d (1956)] which method comprises treating a cycloaliphatic ketone of formula III with the organo-metallic compound obtained by the reaction between an acetylenic alcohol, namely but-1-yn-3-ol, and a halogenomagnesium derivative under the conditions normally used for carrying out a Grignard reaction.

The following reaction scheme shows the aforementioned mode of preparation:

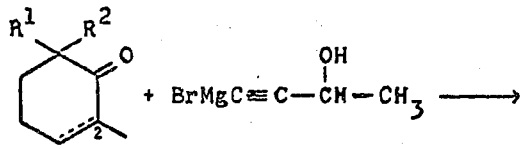

III

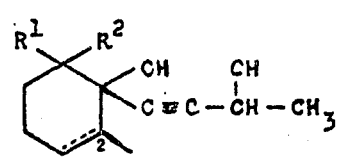

II

According to a modification of the method described above the organo-metallic compound is a lithium derivative obtained by the reaction between but-1-yn-3-ol and a strong lithium base such as n-butyl-lithium, methyl-lithium or phenyl-lithium.

The diols of formula II can equally be prepared by the reaction of but-1-yn-3-ol with ketones III in the presence of a strong base such as an alkali metal alkoxide, e.g. sodium or potassium methoxide, ethoxide or tert-butoxide. Potassium tert-butoxide is preferred.

The diols of formula II obtained according to the method described above occur in a mixture of diastereoisomers The said isomers can be separated by means of the usual techniques such as preparative vapour phase chromatography, fractional distillation or fractional crystallization. However, for practical reasons the mixture resulting directly from the preparation according to the process described above is used for the next reaction step.

By the process of the invention, in addition to the compounds of formula I, there are obtained compounds of formula

IV wherein R¹ and R² have the meaning indicated for formula I. The said compounds occur in the form of two diastereoisomers of formula

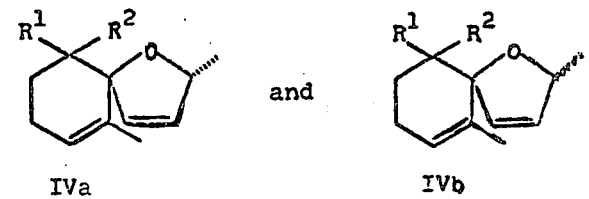

IVa                and                IVb

These isomers can be separated by means of the separation techniques usually employed to this end, e.g. by fractional distillation or preparative vapour phase chromatography. Compounds of formula IV can be separated from the other constituents of the reaction mixture by using the same techniques, the said constituents being, however, mainly represented by compounds I.

Among the compounds whose preparation was made possible by the application of the process of the present invention there is 2-methyl-1-[but-2-enoyl]-cyclohex-1-ene which is a new compound and possesses interesting organoleptic properties.

Equally new are certain diol intermediates of formula II, namely 2-methyl-1-hydroxy-1-[3-hydroxy-but-1-ynyl]-cyclohexane and 2,6,6-trimethyl-1-hydroxy-1-[3-hydroxy-but-1-ynyl]-cyclohex-2-ene.

According to another process of the present invention the alcohols of formula V are prepared by subjecting an ether of formula VI to a rearrangement by the action of a strong base and subsequently of a protic solvent.

A suitable strong base is represented by an organometallic compound which is dissolved or which is in suspension in an inert organic solvent. Typically, there is used an alkyl-lithium such as n-butyl-lithium, hexyl-lithium or isopropyl-lithium, in an ethereal solvent such as ethyl ether, monoglyme, diglyme, dioxan or tetrahydrofuran, or a hydrocarbon such as cyclohexane, hexane, benzene or toluene.

Suitable protic solvents include an alcohol such as methanol, isopropanol or ethanol, or water.

The reaction between the ether of formula VI and the strong base can be carried out at a temperature comprised between about −90 and about +50°C. However, it has been found that the best yields of final product are obtained if temperatures comprised between about −80 and −50°C, preferably of −75°C, are used.

n-Butyl-lithium in ether or tetrahydrofuran is preferably used as the strong base. The preferred protic solvent is water.

Moreover, ether VI is advantageously treated with n-butyl-lithium in the presence of a catalyst, which catalyst is destined to increase the rate of the rearrangement. A class of suitable catalysts includes those substances which are known to increase the efficacy of alkyl-lithium reagents, such as tetramethylethylenediamine [cf. e.g. J. Org. Chem., 29, 2928 (1964)] or potassium tert-butoxide [cf. e.g. J. Organometallic Chem., 8, 9 (1967)].

The alcohols of formula V, some of which are new, possess interesting organoleptic properties and represent useful intermediates for organic synthesis and are particularly interesting in the field of perfumes and flavours. Indeed, by subjecting them to an oxidation according to the usual techniques they lead to the ketones corresponding to formula

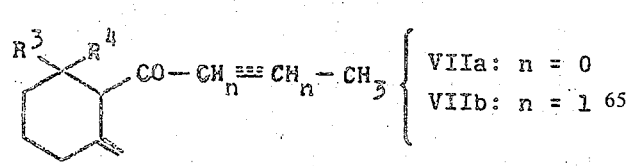

| VIIa: n = 0
| VIIb: n = 1 wherein the dotted lines and the symbols $R^3$, $R^4$ and n have the meaning indicated above, which ketones possess interesting organoleptic properties and can, therefore, be advantageously used as perfuming and/or flavouring ingredients [cf. Swiss patent No. 513,094].

A partial hydrogenation of the acetylenic ketones VIIa may yield the corresponding ethylenic ketone derivatives, VIIb [cf. Swiss patent No. 498,795]. In view of the presence of the ethylenic double bond in the side chain compounds VIIb can possess an isomeric cis- or trans-configuration.

According to the usual procedure the partial hydrogenation can be carried out in the presence of a catalyst of the so-called "Lindlar" type [deactivated Pd/C catalyst, see Helv. Chim. Acta, 35, 446 (1952)].

By the above described method there are obtained compounds VIIb in the form of a mixture comprising the cis- and trans-isomers in a ratio by weight of about 4 : 1. The said isomers can be purified by the usual techniques of separation such as preparative vapour phase chromatography or fractional distillation.

The partial reduction of the acetylenic triple bond of compounds V by means of reagents such as mixed lithium and aluminium hydride, however, leads almost exclusively to the formation of compounds having a trans-configuration.

Thus, e.g., if 2-methylene-6,6-dimethyl-1-[1-hydroxy-but-2-ynyl]-cyclohexane is reduced by means of LiAlH$_4$, trans-2-methylene-6,6-dimethyl-1-[1-hydroxy-but-2-enyl]-cyclohexane is obtained.

The ethers of formula VI, used as starting materials in the process of the invention described above, can be obtained by treating alcohols having the formula

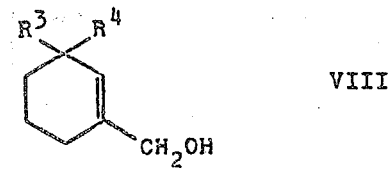

VIII wherein $R^3$ and $R^4$ have the same meaning as that indicated for formula V, with a base such as n-butyl-lithium, hexyl-lithium or isopropyl-lithium, by etherifying the resulting product by means of a but-2-enyl or but-2-ynyl halide.

According to a modification of the synthetic method indicated above, an alcohol having the formula

IX.

containing a double or triple bond in the position indicated by the dotted lines and wherein n stands for zero or 1, is treated with a basic lithium reagent of the type mentioned above, and the resulting product is then etherified by means of a halide having the formula

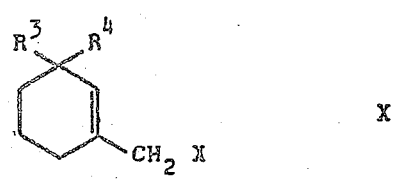

X wherein X represents a halogen such as chlorine or bromine.

Among the compounds whose preparation was made possible by the application of the processes of the present invention there are the compounds of formula

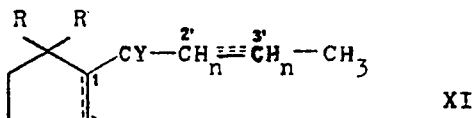

XI a. containing an exocyclic double bond in position 2 of the ring and a triple bond in position 2', and wherein Y represents an oxygen atom or an —OH group and a hydrogen atom, each of the substituents R represents a lower alkyl radical containing from 1 to 6 carbon atoms and n stands for zero; or b. containing a double bond in position 1 of the ring and a double bond in position 2', and wherein Y represents an oxygen atom, each of the substituents R represents a hydrogen atom and n stands for 1.

Specific examples of the compounds of formula XI include 2-methylene-6,6-dimethyl-1-[1-hydroxy-but-2-ynyl]-cyclohexane, 2-methylene-6,6-dimethyl-1-[but-2-ynoyl]-cyclohexane and 2-methyl-1-[but-2-enoyl]-cyclohex-1-ene which are new compounds and possess interesting organoleptic properties.

We have surprisingly found that the above mentioned cycloaliphatic derivatives possess distinct olfactive and flavouring characters and may develop a variety of notes such as the fruity, spicy, leathery notes. They improve the lifting character of the compositions to which they are added and confer freshness to the resulting overall effect achieved by said compositions.

The above mentioned compounds can therefore be used as perfuming and odour-modifying agents in the manufacture of perfumes and perfumed products, and as flavouring and taste-modifying agents for the preparation of artificial flavour compositions and for the aromatization of foodstuffs, animal feeds, beverages, pharmaceutical preparations and tobacco products.

In some cases, they impart to the products, in which they are incorporated, a taste of red berries and can be used for improving the taste and the artificial flavour of strawberry, cranberry, cherry, red-currants or analogous compositions. They may equally develop a fruity taste reminiscent of peach, apricot or even melon. In particular, 2-methyl-1-[but-2-enoyl]-cyclohex-1-ene confers to the fruit base compositions to which it is added a character of dried fruit which may be especially desired by the foodstuff industry in general and by the confectionary in particular.

The proportions in which the new compounds can be used in order to produce an interesting odoriferous effect vary within wide limits. In the preparation of perfume compositions, for example, interesting effects can be obtained by the presence of the new compounds in ratios of about 100 ppm to 5 % of the total of the composition. Depending on the desired odoriferous effects the ratios of these new compounds can be increased to about 10 % and even more.

If the new compounds are used as flavouring agents or as additives destined to modify the organoleptic properties of foodstuffs for men and animals, beverages, pharmaceutical preparations and tobacco, their ratios can also vary within wide limits.

Interesting flavouring effects can e.g. be obtained by the use of 0.1 to 10 ppm of the new compounds, based on the product to be flavoured. However, these ratios can be increased beyond 10 ppm and reach 100 ppm if it is desired to obtain special flavouring effects. In the preparation of flavouring compositions by admixture of the new compounds with other flavouring agents the said compounds can be used in ratios of about 0.1 to 15 % of the total of the composition. In many cases the average of the ratios used lies between 1 and 10 % of the total weight of the composition. It is to be understood that the limits of the proportions given above do not represent absolute limits; in certain cases where special effects are desired the new compounds can be used in higher or lower concentrations than those mentioned above.

The expression "foodstuff" is used in this specification in its broadest sense. It also comprises products such as coffee, tea and chocolate.

The invention is illustrated in a more detailed manner by the following examples, wherein the temperatures are indicated in degrees centigrade.

EXAMPLE 1

2-Methyl-1-[but-2-enoyl]-cyclohex-1-ene 20 g of 50 % aqueous sulphuric acid (parts by weight) were added to 20.2 g (0.11 mole) of 2-methyl-1-hydroxy-1-[3-hydroxy-but-1-ynyl]-cyclohexane and the thus obtained mixture was stirred for 45 minutes at 50°. After having added water to the said mixture, it was extracted three times with pentane, and the combined organic extracts were washed, dried (MgSO$_4$) and concentrated. The resulting residue gave, by fractional distillation, a product of b.p. 118°–120°/12 Torr; 10.9 g (60 %). By purification by means of vapour phase chromatography there was obtained 2-methyl-1-[but-2-enoyl]-cyclohex-1-ene.

IR : 2920, 2850, 1710, 1660, 1435, 1370, 1280, 1250, 970 cm$^{-1}$

NMR : 1.6 (m); 1.84 (q, J$_1$=1 cps, J$_2$=6.5 cps); 2.0 (m); 5.83 (m); 6.09 (m); 6.30–6.80 (m) δ ppm

MS : 164, 149, 135, 121, 107, 95, 93, 91, 79, 77, 69, 67, 55, 44, 41.

2-Methyl-1-hydroxy-1-[3-hydroxy-but-1-ynyl]-cyclohexane used as starting material in the hereinabove preparation can be obtained as follows:

A mixture of 20.0 g of methylcyclohexanone (0.20 mole) and 19.3 g of but-1-yn-3-ol (0.28 mole) was added dropwise within 45 minutes to a suspension maintained at +5° of 20.0 g of potassium tert-butoxide (0.18 mole) in 100 ml of anhydrous ether, and the resulting reaction mixture was maintained at room temperature overnight. After the addition of water, the ethereal phase was separated and the aqueous phase was twice extracted with pentane. The combined organic extracts were washed with water, dried (MgSO$_4$), and the volatile portions were evaporated to yield a residue which, by distillation, gave 25.5 g (70 %) of the desired diol; b.p. 90°–94°/0.02 Torr.

NMR : 1.04 (m); 1.2—2.0 (m); 4.2–4.8 (m) δppm

MS : 182, 164, 149, 135, 125, 121, 112, 111, 108, 107, 97, 95, 93, 91, 81, 80, 79, 77, 69, 68, 67, 66, 55, 53, 45, 44, 43.

EXAMPLE 2

2,6,6-Trimethyl-1-[but-2-enoyl]-cyclohex-1-ene

A mixture of 6.6 g of 30 % aqueous sulphuric acid (parts by weight) and 6.6 g of 2,6,6-trimethyl-1-hydroxy-1-[3-hydroxy-but-1-ynyl]-cyclohexane (32 millimoles) was stirred for 24 hours at 70°. After the addition of water, the reaction mixture was extracted 3 times with ether and the combined organic extracts were washed with water and sodium bicarbonate, dried and concentrated. The resulting residue was distilled to yield 5.4 g of a product of b.p. 114°–117°/12 Torr (yield: 90 %). The distillate by preparative vapour phase chromatography yielded two products. The first one was the desired product whose analytical data were identical with those of a pure sample [cf. French patent No. 1,591,031]. The second one was a mixture of diastereoisomers of theaspirene.

IR : 2840-2990, 1470, 1450, 1380, 1370, 1350, 1115, 1080, 1060, 1000, 980, 910, 870, 860, 810, 750, 710 cm$^{-1}$

NMR : 0.96 (d); 1.23 (d); 1.16 (m); 1.70–2.20 (m); 4.83 (q, broad band); 5.1–5.9 (m) δ ppm

MS : 192, 136, 121, 93, 77, 53, 43, 41, 39.

2,6,6-Trimethyl-1-hydroxy-1-[3-hydroxy-but-1-ynyl]-cyclohexane used as starting material in the above described preparation can be synthesized as follows:

a. 110 ml of a solution of 30 % $H_2O_2$ followed by 28 ml of a 6N aqueous solution of NaOH were added dropwise, while stirring and within 45 minutes and 15 minutes, respectively, to a cooled solution (0°–5°) of 40 g of β-cyclocitral (0.26 mole) in 300 ml of methanol which had been acidified beforehand with 40 drops of concentrated sulphuric acid. The reaction mixture was then kept at room temperature for 3 days, while stirring. After having added water thereto, the said mixture was extracted three times with ether and the combined organic extracts were subjected to the usual treatments of washing (water), drying (MgSO$_4$) and concentration. There were obtained 21.5 g of trimethyl-cyclohexanone by fractional distillation; b.p. 66°–69°/12 Torr (66 %).

b. 130 ml of a 1.65 N solution of n-butyl-lithium in hexane (0.21 mole) were added dropwise within 20 minutes to a solution, kept at −75°, of 7.5 g of but-1-yn-3-ol (0.1 mole) in 50 ml of tetrahydrofuran. The reaction mixture was then kept at room temperature for 30 minutes, then again cooled to −75°. At this temperature there were rapidly added 10 g of trimethyl-cyclohexanone (70 millimoles) dissolved in 25 ml of tetrahydrofuran. Stirring was continued for 30 minutes at −75°, then overnight at room temperature. After having added water thereto, the said mixture was extracted three times with ether and pentane and the combined extracts were subjected to the usual treatments of washing with water, drying over MgSO$_4$ and concentration. The desired product of b.p. 152°–154°/12 Torr was obtained by fractional distillation. 10.0 g (66 %).

NMR : 0.80–1.20 (m); 1.30–2.0 (m); 4.50 (q, broad band) δppm

MS : 210, 177, 167, 152, 151, 149, 135, 123, 121, 109, 107, 95, 93, 91, 87, 84, 82, 81, 79, 77, 75, 69, 67, 57, 56, 55, 53, 45, 44, 43, 41, 39.

EXAMPLE 3

2,6,6-Trimethyl-1-[but-2-enoyl]-cyclohexa-1,3-diene

A mixture of 0.200 g of 2,6,6-trimethyl-1-hydroxy-1-[3-hydroxy-but-1-ynyl]-cyclohex-2-ene, 0.2 ml of 5 % aqueous sulphuric acid (parts by weight) and 0.050 g of mercuric acetate was heated at 50° during 22 h. After cooling, the reaction mixture was poured onto 5 ml of water and then extracted several times with ether. The combined organic extracts were subjected to the usual treatments of washing (water), drying (MgSO$_4$) and concentration to afford a residue which by distillation yielded 0.160 g of a product of b.p. ca. 80°/0.01 Torr containing more than 50 % of the desired ketone.

A pure sample was prepared by purifying it by means of vapour phase chromatography. The analytical data of this pure compound were identical with those of a sample separately prepared according to Helv. Chim. Acta, 53, 541 (1970).

2,6,6-Trimethyl-1-hydroxy-1-[3-hydroxy-but-1-ynyl]-cyclohex-2-ene used as starting material in the hereinabove described process can be synthesized as follows:

133 ml of a 1.75N solution of n-butyl-lithium in hexane (0.233 mole) were added dropwise to a stirred solution of 7.5 g of but-1-yn-3-ol (0.107 mole) in 50 ml of tetrahydrofuran at −75°. The reaction mixture was then kept at room temperature for 30 minutes, then again cooled to −75°. At this temperature there were rapidly added to a solution of 9.85 g of 2,6,6-trimethyl-cyclohex-2-enone [which may be prepared in accordance with the method described in J. Am. Chem. Soc., 77, 5991 (1955)] in 25 ml of tetrahydrofuran (0.071 mole). Stirring was continued for 30 minutes at −75°, then overnight at room temperature. After concentration of the mixture, water was added thereto, and the said mixture was extracted with n-pentane. The combined extracts were then subjected to the usual treatments of washing with water, drying over MgSO$_4$ and concentration to yield a residue which by fractional distillation afforded 12.0 g of the desired diol; b.p. 102°–105°/0.01 Torr; yield 81 %; m.p. 85°–105°.

IR : 3330, 2910, 1660, 1430, 1360, 1235, 1070, 980 cm$^{-1}$

NMR : 1.02 (6H, broad s); 1.42 (3H, d badly resolved); 1.85 (3H, s); 1.2-2.2 (4H, m); 4.54 (1H, m); 5.42 (1H, m) δ ppm MS : m/e: 120 (69); 119 (97); 117 (100); 83 (23); 82 (25); 47 (23).

By carrying out the above process in the absence of mercuric acetate, 2,6,6-trimethyl-1-[but-2-enoyl]-cyclohexa-1,3-diene is obtained at a lower yield.

EXAMPLE 4

2-Methylene-6,6dimethyl-1-[1-hydroxy-but-2-enyl]-cyclohexane

A mixture of 0.97 g of 3,3-dimethyl-1-cyclohex-1-enyl-methyl-crotyl ether in 10 ml of diethyl ether and 1.75 ml of tetramethylethylene-diamine was stirred under nitrogen atmosphere. The temperature was brought to −80° and 9.4 ml of a 1.6N solution of butyl-lithium in hexane were added dropwise within 40 minutes. The mixture was kept at 31 25° for 3 hours and then cooled to −80°, whereupon 10 ml of water were added dropwise, and the whole was stirred until the temperature reached about 20°. The organic layer was separated and the aqueous layer was extracted with two portions of 25 ml each of pentane. The organic extracts were washed three times with 100 ml of water and then dried over anhydrous $K_2CO_3$. The volatile portions were evaporated on the water-bath through a spiral-shaped column of 20 cm length and the obtained residue was distilled under reduced pressure.

By subjecting the crude reaction product to vapour phase chromatography (col. 2.3 m, 15 % CARBOWAX, 135°) or (col. 5 m, 15 % CARBOWAX, 140°) there were isolated 30 % of 2-methylene-6,6-dimethyl-1-[1-hydroxy-but-2-enyl]-cyclohexane (A) having the following constants:

IR : 3460, 2860–3080, 1670, 1640, 1450, 1380, 1160, 1120, 960, 890, 870, 800, 740, 680 $cm^{-1}$
NMR ($CCl_4$) : 0.88, 1.01, (s); 1.45, 1.66, 2.11, 4.20 4.45, 4.79, 5.46 (m) δ ppm
MS : m/e: 194, 139, 124, 109, 95, 81, 71, 55, 41, 27.

From the reaction product there were also isolated 17 % of 6,6-dimethyl-2-[1-hydroxy-2-methyl-but-3-enyl]-cyclohex-1-ene (B), isomer (1), having the following constants:
IR : 3440, 2840–3080, 1640, 1450, 1360, 1280, 1200, and 7.5 ml (10 g) of crotyl bromide. The mixture was vigorously stirred for 3 hours and then periodically cooled in an ice-bath so as to keep its temperature in the vicinity of room temperature. The whole was then poured into water, extracted with pentane and the pentane extracts were treated as usual by washing and drying them. The pentane was removed at atmospheric pressure by means of a spiral-shaped column of 20 cm length, and then the residue was fractionally distilled on a Vigreux column. 7.6 g (78 %) of the desired ether, b.p. 107°–112°/12 Torr, were recovered, purity about 93 % according to the analysis by vapour phase chromatography (col. 2.3 m, 15 % CARBOWAX, 150°).

NMR ($CCl_4$) : 0.96 (s); 1.20–2.10, 3.70 (m); 5.27 (broad s); 5.48 (broad t) δ ppm The rearrangement of 3,3-dimethyl-1-cyclohex-1-enyl-methyl-crotyl ether described in the present example was repeated under various conditions by following, however, the described general method. The Table shown below sums up these conditions and the results obtained. In the said Table the following conventional signs have been used.

| | | | |
|---|---|---|---|
| E(g) | = amount of crotyl ether used | ME (ml) | = organometallic reagent in solution in hexane or pentane |
| S (ml) | = solvent used | | |
| Et | = sulphuric ether | tp (h) | = reaction time |
| THF | = tetrahydrofuran | t (°centigrade) | = reaction temperature |
| MON | = dimethoxyethane | n | = normality |
| C (ml), (g) | = catalyst | nB | = normal butyl-lithium |
| TMEDA | = tetramethylethylenediamine | sB | = secondary butyl-lithium |

| | Reaction conditions | | | | Yields of products % | | |
|---|---|---|---|---|---|---|---|
| EXPERIMENT | E | S | C | ME | tp/t | A | B (1) | B (2) |
| 1 | 0.97 | Et (10) | TMEDA (1.7) | 20 sB; 0.73 n | 2.75/−25 | 25 | 18 | 36 |
| 2 | 0.097 | THF (1) | — | 0.95 nB; 1.6 n | 7/−25 | 32 | 25 | 25 |
| 3 | 0.097 | MON (1) | — | 0.95 nB; 1.6 n | 5/−25 | 13.5 | — | 53 |
| 4 | 0.097 | Et (1) | — | 2 sB; 0.73 n | 8/−25 | 9 | 20 | 34 |
| 5 | 0.097 | THF (1) | — | 2 sB; 0.73 n | 4.5/−25 | 20 | 25 | 27 |
| 6 | 0.097 | MON (1) | — | 2 sB; 0.73 n | 6.5/−25 | 13.5 | 14.5 | 17 |
| 7 | 0.097 | Et (1) | — | 0.95 nB; 1.6 n | 6.5/−25 | 2 | 1 | 1 |
| 8 | 0.3 | THF (4) | t.BuOK (0.39) | 2 nB; 1.6 n | 3/−22 | 31 | 12 | 14.5 |
| 9 | 0.3 | Et (4) | t.BuOK (0.39) | 2 nB; 1.6 n | 3/−22 | 28 | 20 | 15 |

1130, 970-1040, 910, 870, 780 $cm^{-1}$
NMR ($CCl_4$) : 0.97 (s); 1.20–2.10 (m); 2.29 (m); 3.51 (d broad); 4.70–6.10 (m) δ ppm
MS : m/e: 176, 139, 121, 109, 95, 81, 69, 55, 43, 29; and 42 % of 6,6-dimethyl-2-[1-hydroxy-2-methyl-but-3enyl]-cyclohex-1-ene (B), isomer (2), having the following constants:
IR : 3400, 3080, 2820–3000, 1640, 1450, 1360, 1275, 1200, 1130, 970–1040, 940, 910, 870, 770 $cm^{-1}$
NMR ($CCl_4$) : 0.95 (broad s); 1.25–1.60 (m); 3.0 (broad s); 3.60 (broad d); 4.63–6.20 (m) δ ppm
MS : m/e: 176, 139, 121, 109, 95, 81, 69, 55, 43, 29.

The 3,3-dimethyl-1-cyclohex-1-enyl-methyl-crotyl ether used as starting material in the above described preparation was obtained according to the following procedure:

A solution of 7 g of 6,6-dimethyl-2-hydroxymethylcyclohex-1-ene [which can be prepared according to Helv. Chim. Acta, 34, 728 (1951), or J. Am. Chem. Soc., 69, 1361 (1947)] in 30 ml of ether was cooled to −80°. To this solution there were added dropwise within 10 minutes 31 ml of a 1.6N n-butyl-lithium solution in hexane. Stirring was continued for 5 minutes at −80° then the mixture was allowed to stand for 20 minutes at room temperature. It was concentrated under reduced pressure, and to the obtained viscous residue there were added 25 ml of dimethyl sulphoxide

EXAMPLE 5

2-Methylene-6,6-dimethyl-1-[1-hydroxy-but-2-ynyl]-cyclohexane

A mixture of 7.68 g of 3,3-dimethyl-1-cyclohex-1-enyl-methyl-but-2-ynyl ether (40 millimoles), 40 ml of anhydrous ether and 4 ml of tetramethylethylene-diamine was stirred under a nitrogen atmosphere. The temperature was brought to −75° and to the mixture there were added dropwise 40 ml of a 1.7N solution of n-butyl-lithium in hexane (68 millimoles). The mixture was maintained at −75° for 2 hours and then at −30° for 2 hours, and 10 ml of water were added dropwise. The whole was further stirred until the temperature reached about 20°. The organic layer was separated and the aqueous phase was extracted with two portions of 50 ml each of pentane. The combined organic extracts were washed with water and then dried over $MgSO_4$, and finally the volatile portions were removed through a spiral-shaped column under reduced pressure. The resulting residue was purified by fractional distillation; b.p. 50°–52°/0.03 Torr; 4.85 g (63 %). The analysis by means of vapour phase chromatography (1.25 m; 15 % CARBOWAX, 125°) showed that the distillate consisted of a mixture 3:5 of the two diastereoisomers of the desired product of formula

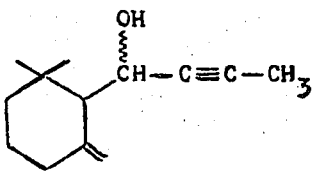

Isomer 1:
IR : 3400, 2920, 2860, 1710, 1660, 1630, 1440, 1380, 1360, 1020, 1000, 900 cm$^{-1}$
NMR : 0.92 (s); 1.00 (s); 1.78 (d, J=2 cps); 4.5 (m); 4.82 (m); 4.98 (m) δ ppm
MS : 192, 149, 124, 123, 122, 121, 109, 107, 95, 93, 91, 81, 79, 77, 69, 67, 55, 44, 43, 41, 39.
Isomer 2:
IR : similar to that of isomer 1
NMR : 0.95 (s); 108 (s); 180 (d, J=2cps); 4.48 (m); 4.67 (m); 4.82 (m) δ ppm
MS : similar to that of isomer 1.

The 3,3-dimethyl-1-cyclohex-1-enyl-methyl-but-2-ynyl ether used as starting product in the above described preparation, can be obtained in accordance with the following procedure:

a. A solution of 1.4 g of 6,6-dimethyl-2-hydroxymethyl-cyclohex-1-ene [which can be prepared according to Helv. Chim. Acta, 34, 728 (1951) or J. Am. Chem. Soc., 69, 1361 (1947)] (10 millimoles) in 5 ml of pentane was cooled to −20°. To this solution there were added, while vigorously stirring, 2.71 g (10 millimoles) of phosphorus tribromide. The reaction mixture was further stirred until it reached room temperature, and then for an additional 30 minutes. The organic phase was then separated, washed with water, with an aqueous solution of sodium bicarbonate, again with water, and dried over anhydrous magnesium sulphate. After evaporation of the volatile portions there was obtained a residue which is directly used for the next reaction step.
NMR : 0.95 (s); 3.76 (s); 5.45 (s, broad band) δ ppm b. A solution of 2.76 g of but-2-ynol (34 millimoles) in 20 ml of ether was cooled to −80°. 20.5 ml (35 millimoles) of a 1.65N solution of n-butyl-lithium in hexane have been added dropwise to the above solution. The reaction mixture was kept, while stirring, for 5 minutes at −80° and then for 20 minutes at room temperature. The volatile portions were evaporated under reduced pressure, and the resulting white solid residue was dissolved in 15 ml of dimethyl-sulphoxide. To the thus obtained solution there were added 7 g (34 millimoles) of 6,6-dimethyl-cyclohex-2-enyl-methyl bromide [prepared according to the method indicated in the above paragraph a)]. The whole was allowed to stand for 2 hours at room temperature, while stirring. The organic phase was separated and the aqueous layer was extracted with pentane. The combined pentane extracts were washed with water, dried over MgSO$_4$ and concentrated by means of a spiral-shaped column. The residue was then distilled by means of a Vigreux column. There were thus obtained 5.3 g of 3,3-dimethyl-cyclohex-1-enyl-methyl-but-2-ynyl ether (81 %); b.p. 116°–117°/12 Torr. An analytical sample was obtained by purification by means of vapour phase chromatography (2.3 m, 15 % CARBOWAX, 140°).
NMR : 0.95 (s); 1.69 (t, J=2 cps); 3.91 (s); 4.07 (q, J=2 cps); 5.50 (s, broad band) δ ppm.

EXAMPLE 6

2-Methylene-6,6-dimethyl-1-[but-2-ynoyl]-cyclohexane 4.85 g of 2-methylene-6,6-dimethyl-1-[1-hydroxybut-2-ynyl]-cyclohexane [which can be prepared according to the method described in example 5] (25 millimoles) in 30 ml of a mixture of ether-hexane 1:1 were added dropwise, while stirring, within 30 minutes to an ice-cooled solution of 24 g of chromic acid (0.25N) in 24 ml of water and 15 ml of a mixture of ether-hexane 1:1. The whole was allowed to stand for 24 hours at room temperature, while stirring vigorously, and then diluted with water. The reaction mixture was extracted with pentane, and the organic extracts, after the usual treatments of washing, drying and concentration, gave a residue which, by fractional distillation under reduced pressure, yielded 3.46 g (72 %) of the desired ketone; b.p. 66°–70°/0.03 Torr. An analytical sample was purified by means of vapour phase chromatography (1.25 m, 15 % CARBOWAX, 130°).
IR : 3080, 2915, 2860, 2810, 1655, 1435, 1380, 1360, 1320, 1230, 1160, 900, 870, 835 cm$^{-1}$
NMR : 0.90 (s); 0.98 (s); 1.98 (s); 3.10 (s); 4.75 (s, broad band); 4.85 (s, broad band) δ ppm
MS : 190, 175, 162, 147, 134, 133, 123, 122, 120, 119, 109, 108, 107, 105, 92, 91, 81, 79, 77, 69, 67, 55, 53, 43, 41, 39.

The obtained product can be subjected to a partial hydrogenation according to known methods in the presence of a catalyst of the so-called "Lindlar" type. There was thus obtained a mixture 4:1 of cis- and trans-2-methylene-6,6-dimethyl-1-[but-2-enoyl]-cyclohexane, respectively.

EXAMPLE 7

A base perfume composition of the "Chypre" type was prepared by admixing the following ingredients (parts by weight):

| | |
|---|---|
| Nonenal at 1 % * | 10 |
| Undecenal at 10 % * | 20 |
| Bergamot | 100 |
| Oak moss absolute at 50 % * | 50 |
| Patchouli oil | 30 |
| Vetyver Bourbon oil | 20 |
| Artificial jasmin oil | 100 |
| Hexylcinnamic aldehyde | 50 |
| Methyl 2-pentyl-3-oxo-cyclopentyl acetate at 10 % * | 10 |
| Citronellol | 50 |
| Artificial rose oil | 100 |
| Neroli bigarade oil | 10 |
| α-Isomethylionone | 100 |
| Muscene at 10 % * | 50 |
| Cyclopentadecanolide at 10 % * | 100 |
| Galbanum at 10 % * | 10 |
| Artificial lily-of-the-valley oil | 100 |
| Coriander oil | 10 |
| Vetyveryl acetate | 20 |
| Citronellyle acetate | 30 |
| Diethylphthalate | 30 |
| | 1000 |

* in diethylphthalate

By adding to 97 g of the above base composition 3 g of 2-methylene-6,6-dimethyl-1-[but-2-ynoyl]-cyclohexane there was obtained a composition possessing by comparison with the base composition a better lifting as well as a natural style of spicy, heady tone. Moreover, the obtained composition possessed a pleasant herbal character reminiscent of laurel or myrtle.

Analogous results, although less powerful, were achieved by adding to the base composition in the same proportions, 2-methylene-6,6-dimethyl-1-[1-hydroxy-but-1-ynyl]-cyclohexane.

EXAMPLE 8

A base perfume composition for after-shave lotion has been prepared by admixing the following ingredients (parts by weight):

| | |
|---|---|
| Menthol | 10 |
| Eugenol | 50 |
| Coumarine | 20 |
| Muscone at 10 % * | 20 |
| Phenyl ethyl alcohol | 120 |
| Lavender oil | 210 |
| Pimento oil | 40 |
| Cinnamon oil | 5 |
| Synth. bergamot | 270 |
| Cyclopentadecanone at 10 % * | 30 |
| Methyl 2-pentyl-3-oxo-cyclopentyl acetate | 20 |
| Absolute oak moss | 15 |
| Benzyle salicylate | 20 |
| Isobutylsalicylate | 30 |
| Geranium Bourbon oil | 70 |
| Musk ketone | 20 |
| Ethyl alcohol | 50 |
| | 1000 |

* in 95 % ethyl alcohol

By adding to 95 g of the hereinabove given base composition 5 g of 2-methyl-1-[but-2-enoyl]-cyclohex-1-ene there is obtained by comparison with the base composition a perfume composition possessing a pleasant and fresh leathery note.

EXAMPLE 9

Preparation of a flavouring composition of the "Tutti-Frutti" type

A flavouring composition of the "Tutti-Frutti" type was prepared by admixing the following ingredients (parts by weight):

| | |
|---|---|
| Vanillin | 20 |
| Allyl caproate | 10 |
| Citral | 20 |
| Amyl butyrate | 35 |
| Orange oil | 45 |
| Ethyl butyrate | 75 |
| Ethyl acetate | 185 |
| Amyl acetate | 185 |
| Lemon oil | 400 |
| Total | 975 |

25 g of 2-methyl-1-[but-2-enoyl]-cyclohex-1-ene were added to 975 g of the above mixture called "test " composition. A "check" composition was prepared by the addition of 25 g of lemon oil to 975 g of the above mixture.

The "test" and "check" compositions were added to the foodstuffs described below in the indicated proportions (100 kg of product to be flavoured):

| | |
|---|---|
| Cake | 20 g |
| Custard | 5 – 10 g |
| Candy | 15 – 20 g |

Candy: 100 ml of sugar syrup (obtained by dissolving one kilogram of sucrose in 600 ml of water) and 20 g of glucose were mixed and slowly heated to 145°. The flavour was added to the mass and the mixture was allowed to cool and harden. Custard: A mixture of 60 g of sucrose and 3 g of pectin were added, while stirring, to 500 ml of warm milk. The mixture was brought to the boiling point for a few seconds and the flavour was added, whereupon the whole was cooled. Cake: The following ingredients were mixed: 100 g of vegetable margarine, 1.5 g of NaCl, 100 g of sucrose, 2 eggs and 100 g of flour. The flavour was added to the above mass and the whole was heated to 180° for 40 minutes.

The samples of finished foodstuff were tasted by a group of experts who had to state their opinion as to the taste of the samples which had been submitted to them. All the members of the group declared that the test samples had a more marked fruity note than that of the check samples and that they moreover possessed a character which was reminiscent of red berries. Moreover, the test samples possessed a character reminiscent of dried fruit.

When 2-methylene-6,6-dimethyl-1-[but-2-ynoyl]-cyclohexane was added instead to the base composition, the effects achieved on the flavoured foodstuffs were analogous; the flavouring character was, however, more fruity, reminiscent of peach or apricot.

We claim:

1. Process for the preparation of compounds of the formula

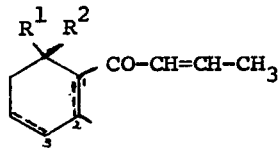

I containing an isolated double bond in position 1 or two conjugated double bonds in position 1 and 3, the double bonds being represented by the dotted lines, and wherein the substituents $R^1$ and $R^2$ may be the same or different and each represents a hydrogen atom or a lower alkyl radical containing from 1 to 6 carbon atoms, which comprises treating a diol having the formula

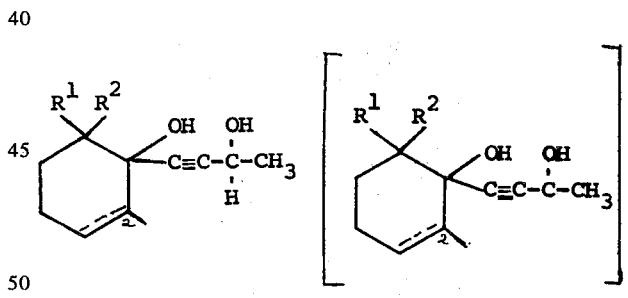

II comprising a saturated or mono-unsaturated six membered ring, the double bond being indicated by the dotted line and wherein $R^1$ and $R^2$ have the meaning indicated above, with phosphoric acid, sulphuric acid, trifluoroacetic acid, p-toluene sulphonic acid, acid diatomaceous earths or an acidic cation exchange resin.

2. Process according to claim 1 in which the diol is treated with diluted sulphuric acid.

3. Process according to claim 1 wherein the reaction between the diol and the acid is carried out in the presence of a salt of copper nickel or mercury.

4. Process according to claim 1 where the reaction is carried out at a temperature of between about 40° and 90°C.

* * * * *

UNITED STATES PATENT AND TRADEMARK OFFICE
CERTIFICATE OF CORRECTION

PATENT NO. : 3,946,078
DATED : March 23, 1976
INVENTOR(S) : Valentin Rautenstrauch and Ferdinand Naf.

Page 1 of 2

It is certified that error appears in the above-identified patent and that said Letters Patent are hereby corrected as shown below:

Column 4, lines 15-24,

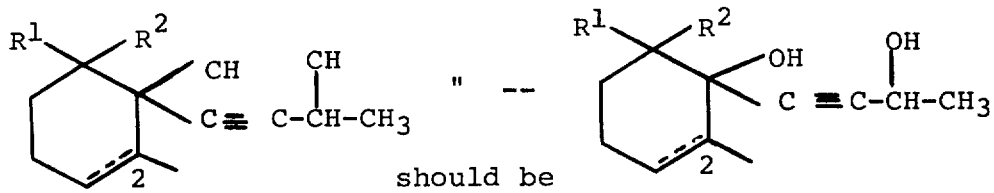

should be

Column 6, line 53, "$CH_n \equiv CH_n$-$CH_2OH$    IX." should be

--$CH_n \equiv CH_n$-$CH_2OH$    IX.--.

Column 9, line 31, "6N" should be --6$\underline{N}$--.

Column 9, line 47, "N" should be --$\underline{N}$--.

Column 10, line 25, "1.75N" should be --1.75$\underline{N}$--.

Column 10, line 56, "2-Methylene-6,6dimethyl-1-[1-hydroxy-but-2-enyl]-cyclohexane"
should be --2-Methylene-6,6-dimethyl-1-[1-hydroxy-but-2-enyl]-cyclohexane--.

Column 10, line 62, "6N" should be --6$\underline{N}$--.

Column 10, line 64, "The mixture was kept at 31 25° for 3 hours and" should be
--The mixture was kept at -25° for 3 hours and--.

UNITED STATES PATENT AND TRADEMARK OFFICE
CERTIFICATE OF CORRECTION

PATENT NO. : 3,946,078
DATED : March 23, 1976
INVENTOR(S) : Valentin Rautenstrauch and Ferdinand Naf It is certified that error appears in the above-identified patent and that said Letters Patent are hereby corrected as shown below:

Column 11, line 63, "6N" should be --6$\underline{N}$--.

Column 12, line 51, "7N" should be --7$\underline{N}$--.

Column 13, line 10, "Isomer 1" should be --Isomer $\underline{1}$--.

Column 13, line 17, "Isomer 2" should be --Isomer $\underline{2}$--.

Column 13, line 44, "65N" should be --65$\underline{N}$--.

Column 14, line 12, "0.25N" should be --0.25$\underline{N}$--.

Column 14, line 53, "Muscene at 10%" should be --Muscone at 10%--.

Column 16, lines 40-50, Please delete formula in brackets.

Signed and Sealed this

Fifth Day of October 1976

[SEAL]

Attest:

RUTH C. MASON
Attesting Officer

C. MARSHALL DANN
Commissioner of Patents and Trademarks